(12) United States Patent
Yun et al.

(10) Patent No.: US 10,502,464 B2
(45) Date of Patent: Dec. 10, 2019

(54) APPARATUS FOR REMOVING RESIDUAL WATER IN HOT WATER MAT USING CIRCULATING PUMP

(71) Applicant: KYUNGDONG NAVIEN CO., LTD., Pyeongtaek-si (KR)

(72) Inventors: Tae Won Yun, Seoul (KR); Hyung Geol Im, Seoul (KR); Yong Seok Lee, Seoul (KR)

(73) Assignee: KYUNGDONG NAVIEN CO., LTD., Pyeongtaek (KR)

( * ) Notice: Subject to any disclaimer, the term of this patent is extended or adjusted under 35 U.S.C. 154(b) by 254 days.

(21) Appl. No.: 15/601,456

(22) Filed: May 22, 2017

(65) Prior Publication Data

US 2017/0336110 A1 Nov. 23, 2017

(30) Foreign Application Priority Data

May 23, 2016 (KR) .................. 10-2016-0062686

(51) Int. Cl.
*A61F 7/08* (2006.01)
*A61M 1/00* (2006.01)
(Continued)

(52) U.S. Cl.
CPC ............... *F25B 30/04* (2013.01); *A61F 7/08* (2013.01); *A61M 1/0084* (2013.01); *F24D 3/082* (2013.01)

(58) Field of Classification Search
CPC ........ A61F 7/08; A61M 1/0084; F24D 3/082; F25B 30/04
(Continued)

(56) References Cited

FOREIGN PATENT DOCUMENTS

CN 106016437 A * 10/2016
KR 10-1541745 B1 8/2015

OTHER PUBLICATIONS

Oh Suk Ho et al., "CN106016437A English Machine Translation.pdf", Oct. 12, 2016—Machine translation from Espacenet.com.*

* cited by examiner

*Primary Examiner* — Levon J Shahinian
(74) *Attorney, Agent, or Firm* — STIP Law Group, LLC

(57) ABSTRACT

Provided is an apparatus for removing residual water in a hot water mat using a circulating pump, in which residual water that remains in a boiler and a mat of the hot water mat and a mat can be conveniently and rapidly removed, the configuration of the apparatus for removing residual water in the hot water mat can be simplified and the leakage at a connector of the boiler and the mat is prevented from occurring so that the risk of suffering a low-temperature burn can be eliminated during the removal of residual water. The apparatus for removing residual water in a hot water mat, the hot water mat including a boiler (100) for supplying hot water by heating water and a mat (200) in which heating is performed by using hot water heated by the boiler (100) as a heat source, includes: a circulating pump (120) provided in the boiler (100) and configured to pump water to be circulated between the boiler (100) and the mat (200); a boiler connector (140) including a boiler-side discharge connector (141) and boiler-side water return connectors (142, 143), which are connected to the boiler (100); a mat connector (220) including a mat-side discharge connector (221) and mat-side water return connectors (222, 223), which are connected to the mat (200); and a residual water removing connector (300) coupled between the boiler connector (140) and the mat connector (220) and including a residual water outlet (340) through which water flowing through the boiler-side discharge connector (141) is discharged.

11 Claims, 6 Drawing Sheets

(51) Int. Cl.
*F24D 3/08* (2006.01)
*F25B 30/04* (2006.01)

(58) Field of Classification Search
USPC .............................................. 134/19, 166 C
See application file for complete search history.

【FIG. 1】
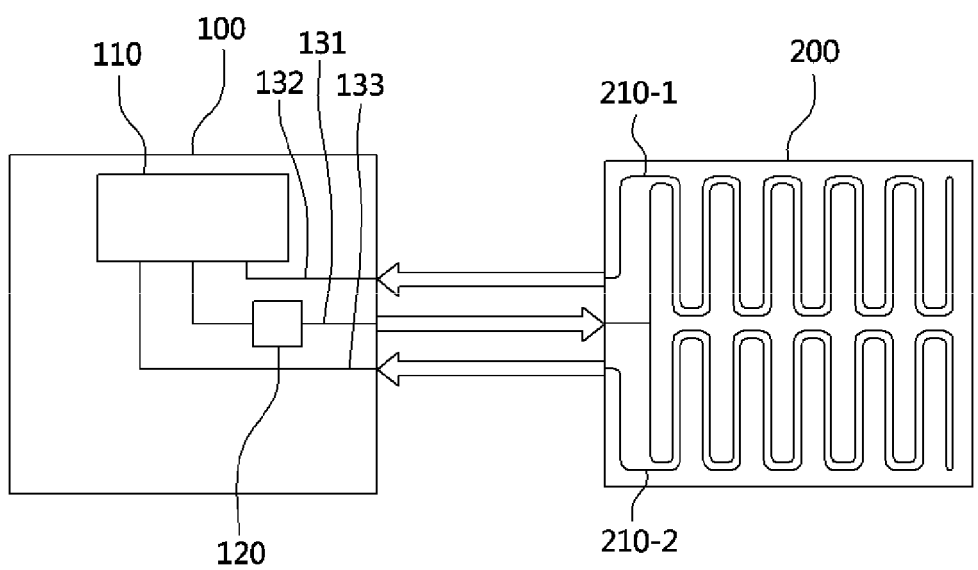

[FIG. 2]
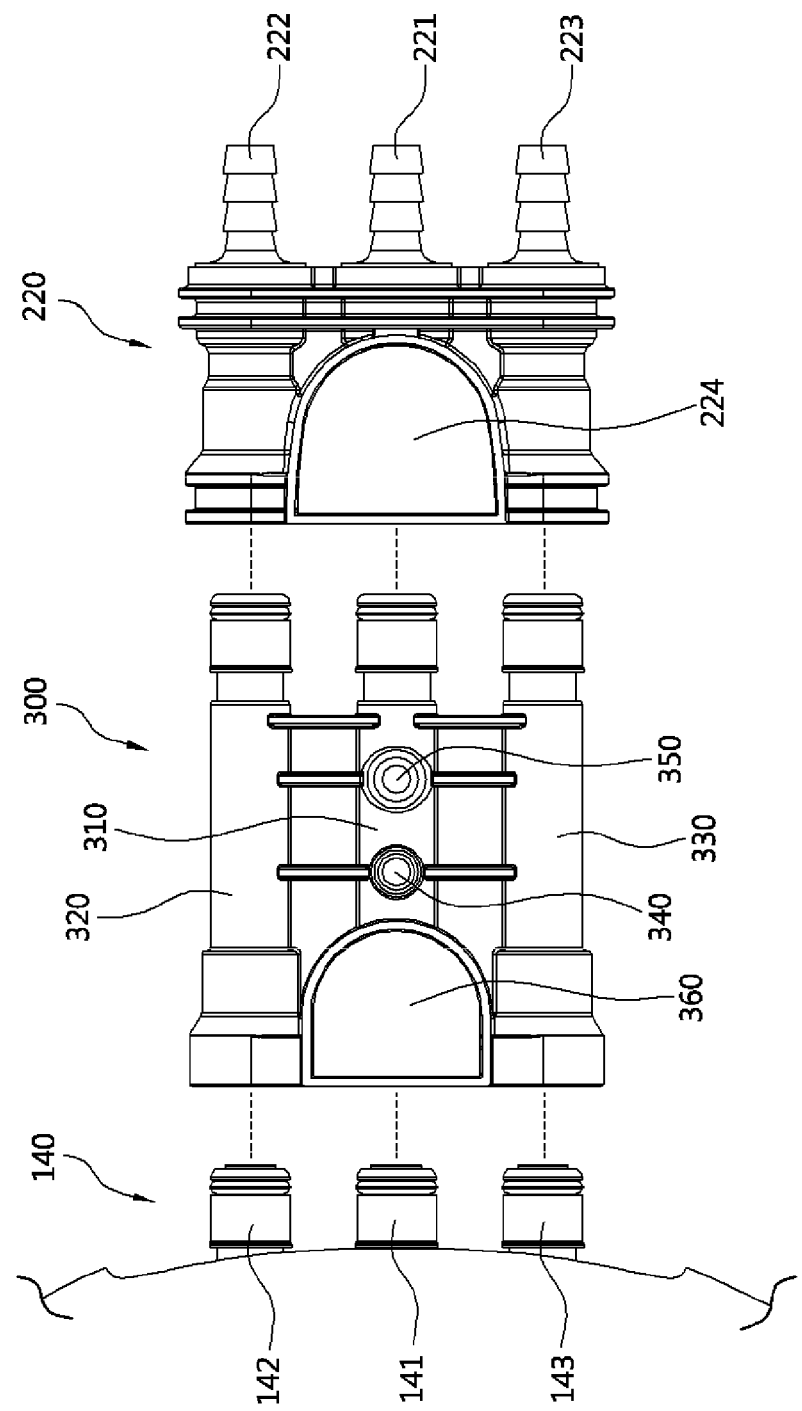

【FIG. 3】
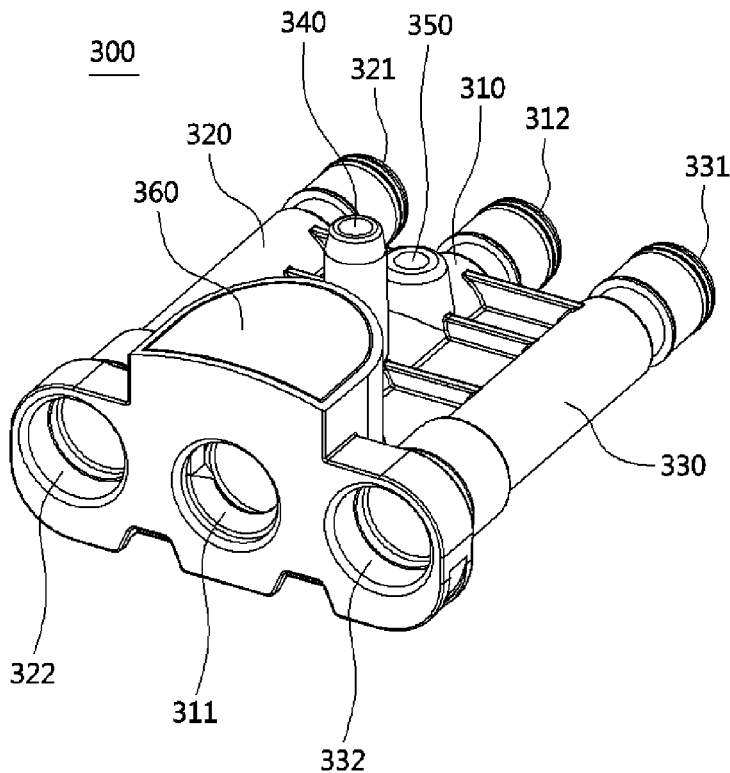
【FIG. 4】
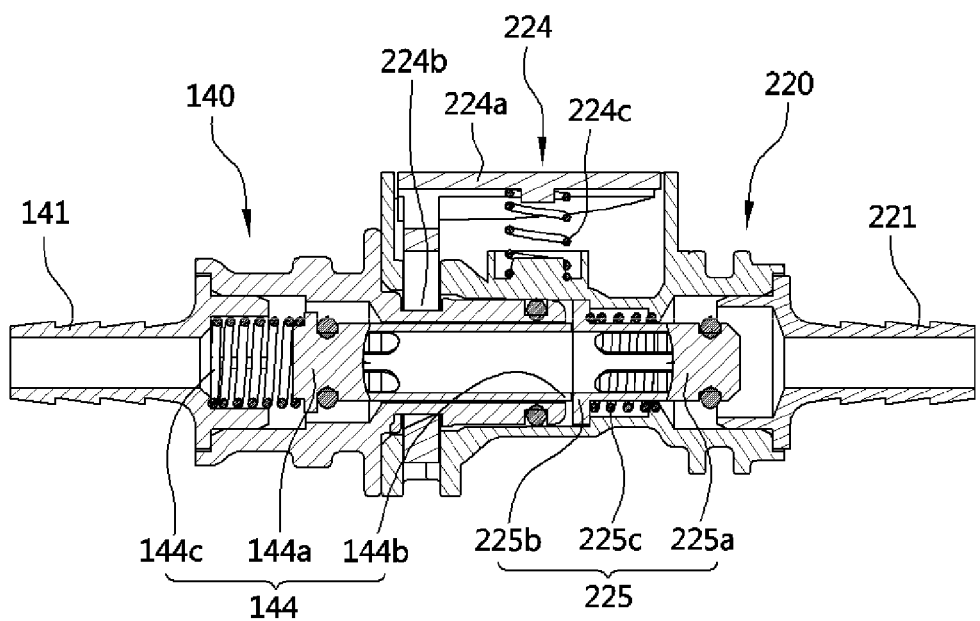

[FIG. 5A]
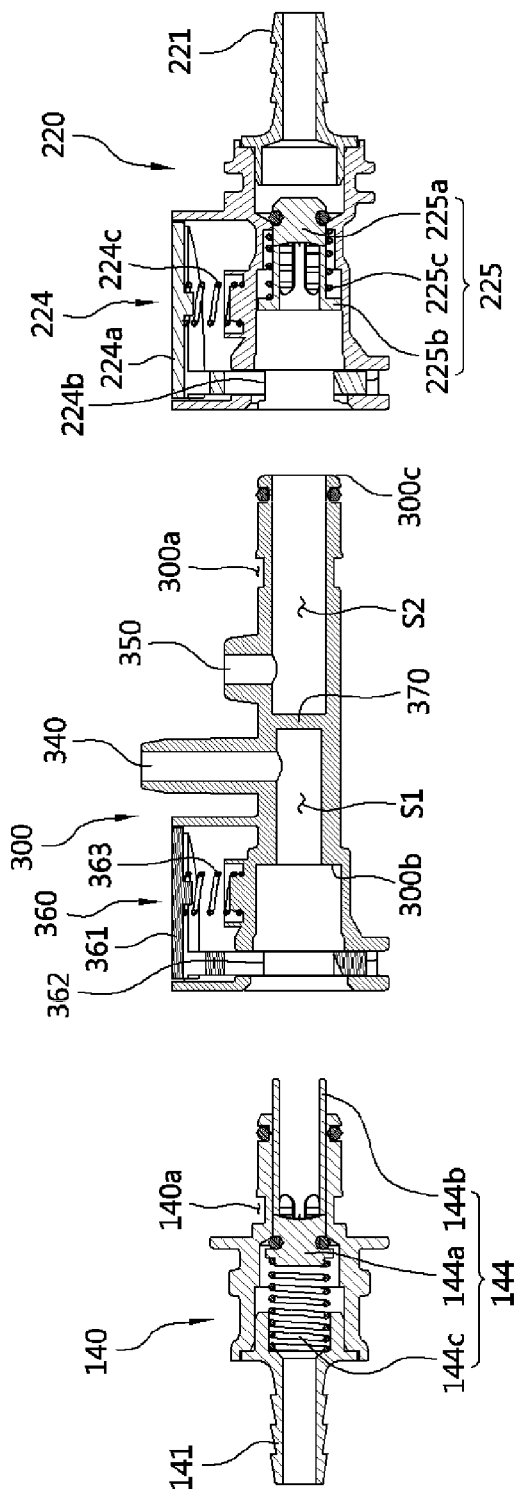

【FIG. 5B】
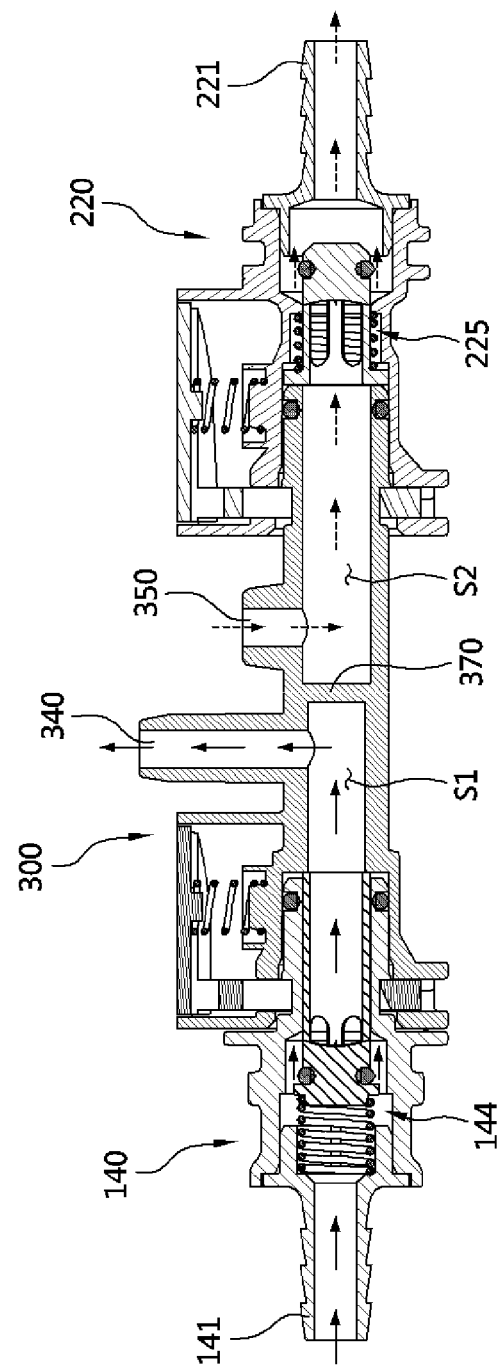

[FIG. 6]
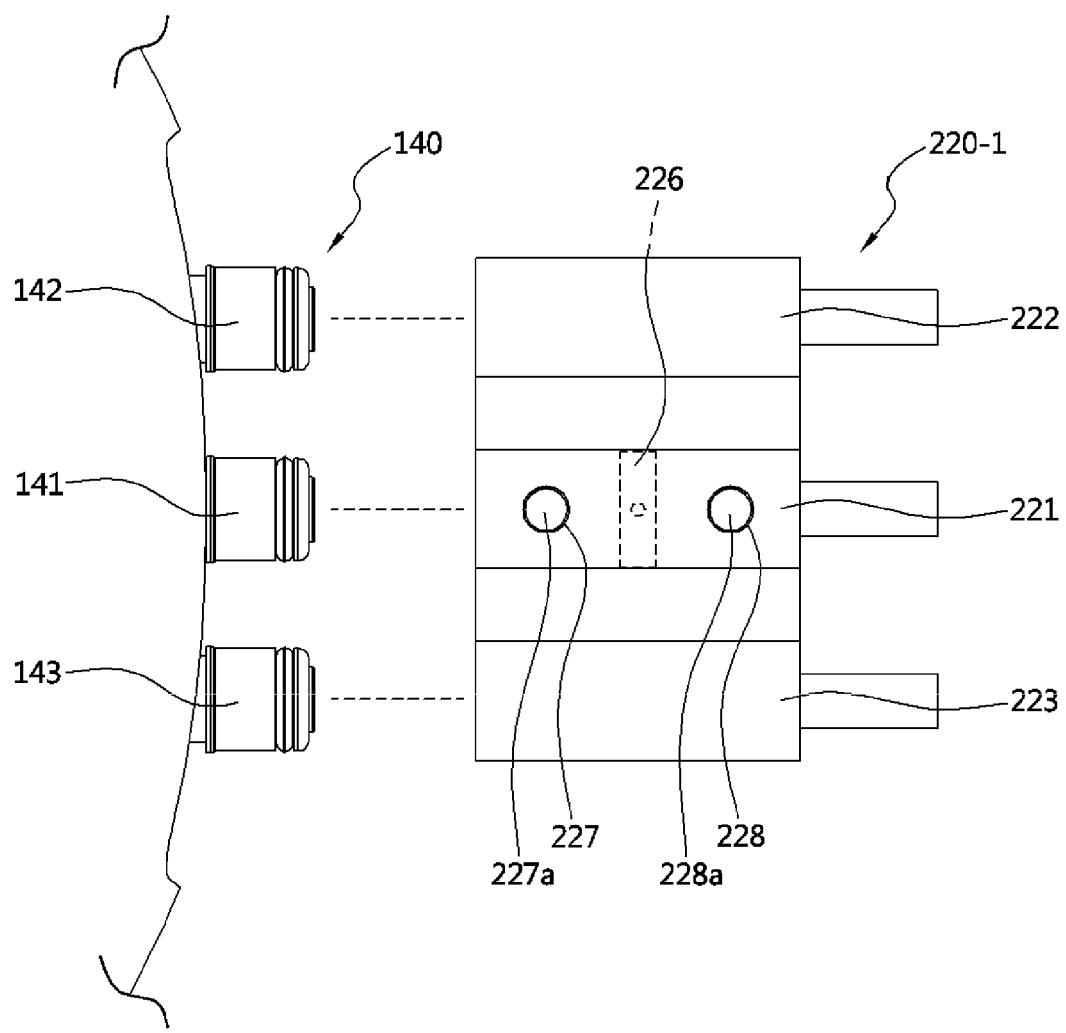

APPARATUS FOR REMOVING RESIDUAL WATER IN HOT WATER MAT USING CIRCULATING PUMP

CROSS-REFERENCE TO RELATED APPLICATIONS

This application claims the priority of the Korean Patent Application NO 10-2016-0062686 filed on May 23, 2016, in the Korean Intellectual Property Office, the disclosure of which is incorporated herein by reference.

BACKGROUND

1. Field of the Invention

The present invention relates to an apparatus for removing residual water in a hot water mat using a circulating pump, and more particularly, to an apparatus for removing residual water in a hot water mat using a circulating pump, in which residual water in a boiler and a mat can be automatically removed using the circulating pump provided in the boiler of the hot water mat.

2. Discussion of Related Art

Generally, a hot water mat includes a boiler for supplying hot water by heating water, and a mat in which heating is performed by using hot water heated by the boiler as a heat source.

A circulating pump is provided inside the boiler so as to circulate hot water between the boiler and the mat. The prior art relating to a hot water mat that performs heating by circulating hot water between a boiler and a mat through an operation of the circulating pump, is disclosed in Korean Patent Registration No. 10-1541745.

Meanwhile, a conventional hot water mat uses tap water and purified water through periodic water replenishment. In addition, water in the boiler and the mat has to be removed so that water in the boiler and the mat can be serviced after the use season for using the hot water mat has passed or during use.

In the related art, as a way to remove water in the boiler and the mat, water in the boiler and the mat is removed by applying pneumatic pressure using a manual hand pump or the like.

However, in the conventional method of removing residual water, it is difficult for the elderly or people with physical ailments to remove residual water using the manual pump. In addition, it takes a long time to remove water in a manual manner, and when residual water is removed using an air injecting pump, there is a problem in that it is troublesome to additionally connect a separate pump to the air injecting pump, and a problem of an increase in costs. When high-temperature hot water is removed in the manual manner, a worker may be exposed to the risk of suffering low-temperature burns due to the leakage of hot water.

SUMMARY OF THE INVENTION

The present invention is directed to an apparatus for removing residual water in a hot water mat using a circulating pump, in which residual water that remains in a boiler and a mat of the hot water mat can be conveniently and rapidly removed, the configuration of the apparatus for removing residual water in the hot water mat can be simplified and the leakage at a connector of the boiler and the mat is prevented from occurring so that the risk of suffering a low-temperature burn can be eliminated during the removal of residual water.

According to an aspect of the present invention, there is provided an apparatus for removing residual water in a hot water mat, the hot water mat including a boiler (100) for supplying hot water by heating water and a mat (200) in which heating is performed by using hot water heated by the boiler (100) as a heat source, the apparatus including: a circulating pump (120) provided in the boiler (100) and configured to pump water to be circulated between the boiler (100) and the mat (200); a boiler connector (140) including a boiler-side discharge connector (141) and boiler-side water return connectors (142, 143), which are connected to the boiler (100); a mat connector (220) including a mat-side discharge connector (221) and mat-side water return connectors (222, 223), which are connected to the mat (200); and a residual water removing connector (300) coupled between the boiler connector (140) and the mat connector (220) and including a residual water outlet (340) through which water flowing through the boiler-side discharge connector (141) is discharged.

The air inlet (350) may be formed in the residual water removing connector (300) and may communicate with the mat-side discharge connector (221).

The residual water removing connector (300) may include: a discharge and air inlet (310) connected between the boiler-side discharge connector (141) and the mat-side discharge connector (221) and having the residual water outlet (340) and the air inlet (35) disposed therein; and return portions (320, 330) connected between the boiler-side water return connectors (142, 143) and the mat-side water return connectors (222, 223) and configured to provide a flow path for water returning to the boiler (100) from the mat (200).

A residual water discharge flow path (S1) that communicates with the boiler-side discharge connector (141) and the residual water outlet (340), and an air inlet flow path (S2) that communicates with the air inlet (350) and the mat-side discharge connector (221) may be formed inside the discharge and air inlet (310).

A barrier wall (370) for blocking fluid communication between the residual water discharge flow path (S1) and the air inlet flow path (S2) may be provided inside the discharge and air inlet (310).

The boiler connector (140) may include a first valve (144) that opens a flow path inside the boiler connector (140) in a state in which the boiler connector (140) is coupled to the mat connector (220) or the residual water removing connector (300) and that closes the flow path inside the boiler connector (140) in a state in which the boiler connector (140) is separated from the mat connector (220) or the residual water removing connector (300).

The mat connector (220) may include a second valve (225) that opens a flow path inside the mat connector (220) in a state in which the mat connector (220) is coupled to the boiler connector (140) or the residual water removing connector (300) and that closes the flow path inside the mat connector (220) in a state in which the mat connector (220) is separated from the boiler connector (140) or the residual water removing connector (300).

A connection portion between the boiler connector (140) and the residual water removing connector (300) may include a first connector detachable portion (360) that is elastically supported to be engaged with the boiler connector (140) and the residual water removing connector (300) when the boiler connector (140) and the residual water removing connector (300) are coupled to each other and that is operated so that the engagement between the boiler connector (140) and the residual water removing connector (300) is released by a pressing operation of a user when the boiler connector (140) and the residual water removing connector (300) are separated from each other.

A connection portion between the residual water removing connector (300) and the mat connector (220) may include a second connector detachable portion (224) that is elastically supported to be engaged with the residual water removing connector (300) and the mat connector (220) when the residual water removing connector (300) and the mat connector (220) are coupled to each other, and that is operated so that the engagement between the residual water removing connector (300) and the mat connector (220) is released by a pressing operation of the user when the residual water removing connector (300) and the mat connector (220) are separated from each other.

According to another aspect of the present invention, there is provided an apparatus for removing residual water in a hot water mat, the hot water mat including a boiler (100) for supplying hot water by heating water and a mat (200) in which heating is performed by using hot water heated by the boiler (100) as a heat source, the apparatus including: a circulating pump (120) provided in the boiler (100) and configured to pump water to be circulated between the boiler (100) and the mat (200); a boiler connector (140) including a boiler-side discharge connector (141) and boiler-side water return connectors (142, 143), which are connected to the boiler (100); and a mat connector (220-1) including a mat-side discharge connector (221) and mat-side water return connectors (222, 223), which are connected to the mat (200), wherein the boiler-side discharge connector (141) or the mat-side discharge connector (221) includes a gate (226) that opens/closes a flow path inside the boiler-side discharge connector (141) or the mat-side discharge connector (221), a residual water outlet (227) disposed at one side of the gate (226), and a first opening/closing valve (227a) that opens/closes the residual water outlet (227).

The boiler-side discharge connector (141) or the mat-side discharge connector (221) may include an air inlet (228) disposed at the other side of the gate (226) and a second opening/closing valve (228a) that opens/closes the air inlet (228).

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which:

FIG. 1 is a block diagram schematically illustrating a configuration of a boiler and a mat of a hot water mat according to an embodiment of the present invention;

FIG. 2 is a plan view showing a structure in which a residual water removing connector is installed between a boiler connector and a mat connector of a hot water mat according to an embodiment of the present invention;

FIG. 3 is a perspective view of the residual water removing connector illustrated in FIG. 2;

FIG. 4 is a cross-sectional view showing a state in which the boiler connector and the mat connector of the hot water mat are coupled to each other;

FIGS. 5A and 5B are cross-sectional views showing a state in which the boiler connector, the residual water removing connector, and the mat connector of the hot water mat are separated from each other and a state in which they are coupled to each other, respectively; and FIG. 6 is a plan view of an apparatus for removing residual water in a hot water mat according to another embodiment of the present invention.

DETAILED DESCRIPTION OF EXEMPLARY EMBODIMENTS

Configurations and operations in exemplary embodiments of the present invention will be described in detail below with reference to the accompanying drawings.

An apparatus for removing residual water in a hot water mat using a circulating pump according to the present invention, the hot water mat including a boiler 100 for supplying hot water by heating water and a mat 200 in which heating is performed by using hot water heated by the boiler 100 as a heat source, the apparatus includes a circulating pump 120 provided in the boiler 100 and pumping water to be circulated between the boiler 100 and the mat 200, a boiler connector 140 including a boiler-side discharge connector 141 and boiler-side water return connectors 142 and 143, which are connected to the boiler 100, a mat connector 220 including a mat-side discharge connector 221 and mat-side water return connectors 222 and 223, which are connected to the mat 200, and a residual water removing connector 300 coupled between the boiler connector 140 and the mat connector 220 and including a residual water outlet 340 through which water flowing through the boiler-side discharge connector 141 is discharged. An air inlet 350 may be formed in the residual water removing connector 300 and may communicate with the mat-side discharge connector 221.

Referring to FIG. 1, the hot water mat according to the present invention includes the boiler 100 for supplying hot water by heating and storing water, and the mat 200 in which heating is performed using hot water heated by the boiler 100 as a heat source.

The boiler 100 includes a water tank 110 for heating and storing water, and the circulating pump 120 for supplying water stored in the water tank 110 to the mat 200 and pumping water that circulates in the mat 200 to be returned to the boiler 100.

The boiler 100 further includes an outlet pipe 131 that provides a flow path through which water in the water tank 110 is supplied to the mat 200, and water return pipes 132 and 133 that provides a flow path through which water passing through the mat 200 is returned to the water tank 110.

Hot water pipes 210-1 and 210-2 through which hot water is circulated are installed in the mat 200. In the current embodiment, the hot water pipes 210-1 and 210-2 are divided into a first hot water pipe 210-1 and a second hot water pipe 210-2 so that separate heating of the mat 200 can be performed. However, the hot water pipes 210-1 and 210-2 may be configured as a single pipe structure.

Referring to FIGS. 2 and 3, the boiler connector 140 is provided at one side of the boiler 100, and the mat connector 220 is provided at one side of the mat 200. The boiler connector 140 and the mat connector 220 have an interconnectable structure in which a circulating flow path through which water is discharged and returned is formed between the boiler 100 and the mat 200.

The boiler connector 140 includes the boiler-side discharge connector 141 and the boiler-side water return connectors 142 and 143. The boiler-side discharge connector 141 forms a flow path for water supplied from the boiler 100 to the mat 200, and the boiler-side water return connectors 142 and 143 form a flow path for water returning to the boiler 100 from the mat 200.

The mat connector 220 includes a mat-side discharge connector 221 and mat-side water return connectors 222 and 223. The mat-side discharge connector 221 forms a flow path for water supplied from the boiler 100 to the mat 200, and the mat-side water return connectors 222 and 223 form a flow path for water returning to the boiler 100 from the mat 200.

In an embodiment, for a structure capable of performing separate heating, the boiler-side water return connectors 142 and 143 may include a boiler-side first return connector 142 and a boiler-side second return connector 143, and the mat-side water return connectors 222 and 223 may include a mat-side first return connector 222 and a mat-side second return connector 223.

In another embodiment, each of the boiler-side water return connectors 142 and 143 and the mat-side water return connectors 222 and 223 may also be configured as a single structure.

The residual water removing connector 300 includes a discharge and air inlet 310, which is detachably coupled between the boiler connector 140 and the mat connector 220, is connected between the boiler-side discharge connector 141 and the mat-side discharge connector 221 and has the residual water outlet 340 and the air inlet 350 therein, and return portions 320 and 330, which are connected between the boiler-side water return connectors 142 and 143 and the mat-side water return connectors 222 and 223 and provide a flow path for water returning to the boiler 100 from the mat 200.

A discharge inlet 311 connected to the boiler-side discharge connector 141, and return outlets 322 and 332, which are connected to the boiler-side water return connectors 142 and 143, respectively, are formed at one side of the residual water removing connector 300. An air outlet 312 connected to the mat-side discharge connector 221, and return inlets 321 and 331, which are connected to the mat-side water return connectors 222 and 223, respectively, are formed at the other side of the residual water removing connector 300.

The residual water outlet 340 through which water flowing through the boiler-side discharge connector 141 is discharged, and the air inlet 350 that communicates with the mat-side discharge connector 221, are formed in the discharge and air inlet 310.

Referring to FIGS. 5A and 5B, a residual water discharge flow path S1 that communicates with the boiler-side discharge connector 141 and the residual water outlet 340, and an air inlet flow path S2 that communicates with the air inlet 350 and the mat-side discharge connector 221 are formed inside the discharge and air inlet 310, and a barrier wall 370 for blocking fluid communication between the residual water discharge flow path S1 and the air inlet flow path S2 is provided in the discharge and air inlet 310.

Referring to FIGS. 4, 5A and 5B, the boiler connector 140 includes a first valve 144 that opens a flow path inside the boiler connector 140 in a state in which the boiler connector 140 is coupled to the mat connector 220 (see FIG. 4) or the residual water removing connector 300 (see FIG. 5B) and that closes the flow path inside the boiler connector 140 in a state in which the boiler connector 140 is separated from the mat connector 220 or the residual water removing connector 300 (see FIG. 5A).

The first valve 144 includes a valve sheet 144a that opens/closes the flow path inside the boiler connector 140, an extension 144b that extends from an end of the valve sheet 144a toward one side, and an elastic member 144c that elastically supports the valve sheet 144a in a direction in which the flow path inside the boiler connector 140 is closed.

The mat connector 220 includes a second valve 225 that opens a flow path inside the mat connector 220 in a state in which the mat connector 220 is coupled to the boiler connector 140 (see FIG. 4) or the residual water removing connector 300 (see FIG. 5B) and that closes the flow path inside the mat connector 220 in a state in which the mat connector 220 is separated from the boiler connector 140 or the residual water removing connector 300 (see FIG. 5A).

The second valve 225 includes a valve sheet 225a that opens/closes the flow path inside the mat connector 220, an extension 225b that extends from an end of the valve sheet 225a toward one side, and an elastic member 225c that elastically supports the valve sheet 225a in a direction in which the flow path inside the mat connector 220 is closed.

Referring to FIG. 4, in a state in which the boiler connector 140 and the mat connector 220 are coupled to each other, the extension 144b of the first valve 144 and the extension 225b of the second valve 225 are in contact with each other. In this case, the valve sheet 144a of the first valve 144 and the valve sheet 225a of the second valve 225 are pushed in a direction opposite to a direction in which an elastic force of each of the elastic members 144c and 225c acts, and are moved so that the flow path inside the boiler connector 140 and the flow path inside the mat connector 220 are open.

Referring to both FIGS. 5A and 5B, in a state in which the boiler connector 140 and the residual water removing connector 300 are coupled to each other, the valve sheet 144a connected to the extension 144b when the extension 144b of the first valve 144 is engaged with an engaging protrusion 300b formed at an inner wall of the residual water removing connector 300, is pushed in the direction opposite to the direction in which the elastic force of the elastic member 144c acts, and is moved so that the flow path inside the boiler connector 140 is opened.

In a state in which the mat connector 220 and the residual water removing connector 300 are coupled to each other, the extension 225b of the second valve 225 is in contact with one end 300c of the residual water removing connector 300. In this case, the valve sheet 225a of the second valve 225 is pushed in the direction opposite to the direction in which the elastic force of the elastic member 225c acts, and is moved so that the flow path inside the mat connector 220 is opened.

On the contrary, as illustrated in FIG. 5A, when the boiler connector 140 is separated from the mat connector 220 or the residual water removing connector 300, the valve sheet 144a of the first valve 144 is in close contact with the inner wall of the boiler connector 140 due to the elastic force of the elastic member 144c and thus closes the flow path inside the boiler connector 140. Thus, the leakage of water through the boiler connector 140 is prevented from occurring.

When the mat connector 220 is separated from the boiler connector 140 or the residual water removing connector 300, the valve sheet 225a of the second valve 225 is in close contact with the inner wall of the mat connector 220 due to the elastic force of the elastic member 225c and thus closes the flow path inside the mat connector 220. Thus, the leakage of water through the mat connector 220 is prevented from occurring.

A connection portion between the boiler connector 140 and the residual water removing connector 300 includes a first connector detachable portion 360 that is elastically supported to be engaged with the boiler connector 140 and the residual water removing connector 300 when the boiler connector 140 and the residual water removing connector 300 are coupled to each other and that is operated so that the engagement between the boiler connector 140 and the residual water removing connector 300 is released by a pressing operation of a user when the boiler connector 140 and the residual water removing connector 300 are separated from each other.

The first connector detachable portion 360 includes a pressing portion 361, an engaging portion 362 that is interlocked in a direction opposite to a direction of movement of the pressing portion 361 due to an operation of a lever, and an elastic member 363 that elastically supports the pressing portion 361. An engaging groove 140a in which a distal end of the engaging portion 362 is engaged, is formed in an outside surface of the boiler connector 140 along a circumferential direction.

Thus, when the boiler connector 140 is inserted into an inside of the residual water removing connector 300 and is coupled to the residual water removing connector 300, the engaging portion 362 is seated in the engaging groove 140a, and due to an elastic force of the elastic member 363, the engaging portion 362 is maintained in a close contact state with the engaging groove 140a so that the boiler connector 140 and the residual water removing connector 300 are not arbitrarily separated from each other and can be maintained in a coupled state. When the boiler connector 140 and the residual water removing connector 300 are separated from each other, if the user presses the pressing portion 361 in a downward direction, the engaging portion 362 is moved to an outside of the engaging groove 140a. In this case, the boiler connector 140 can be taken out of the residual water removing connector 300 and separated therefrom.

In addition, in a similar configuration, a connection portion between the residual water removing connector 300 and the mat connector 220 includes a second connector detachable portion 224 that is elastically supported to be engaged with the residual water removing connector 300 and the mat connector 220 when the residual water removing connector 300 and the mat connector 220 are coupled to each other, and that is operated so that the engagement between the residual water removing connector 300 and the mat connector 220 is released by a pressing operation of the user when the residual water removing connector 300 and the mat connector 220 are separated from each other.

The second connector detachable portion 224 includes a pressing portion 224a, an engaging portion 224b that is interlocked in a direction opposite to a movement direction of the pressing portion 224a due to an operation of the lever, and an elastic member 224c that elastically supports the pressing portion 224a. An engaging groove 300a with which a distal end of the engaging portion 224b is engaged is formed in an outside surface of the residual water removing connector 300 along a circumferential direction.

Thus, when the residual water removing connector 300 is inserted into an inside of the mat connector 220 and is coupled to the mat connector 220, the engaging portion 224b is seated in the engaging groove 300a, and due to an elastic force of the elastic member 224c, the engaging portion 224b is maintained in a close contact state with the engaging groove 300a so that the residual water removing connector 300 and the mat connector 220 are not arbitrarily separated from each other and are coupled to each other. When the residual water removing connector 300 and the mat connector 220 are separated from each other, if the user presses the pressing portion 224a in a downward direction, the engaging portion 224b is moved to an outside of the engaging groove 300a. In this case, the residual water removing connector 300 can be taken out of the mat connector 220 and separated therefrom.

Hereinafter, an operation of removing residual water from the hot water mat according to an embodiment will be described.

First, the boiler connector 140 and the mat connector 220 are separated from each other, as shown in FIG. 5A, from a state in which the boiler connector 140 and the mat connector 220 are connected to each other, as shown in FIG. 4. In this case, because, due to an operation of the first valve 144 and the second valve 225, flow paths formed inside the boiler connector 140 and the mat connector 220 are each closed, the leakage of water can be prevented from occurring and an accident, such as a low-temperature burn, can be prevented.

The residual water removing connector 300 is coupled between the boiler connector 140 and the mat connector 220, as shown in FIG. 5B. In this case, due to an operation of the first valve 144 and the second valve 225, the flow paths formed inside the boiler connector 140 and the mat connector 220 are each open.

Next, when the circulating pump 120 provided inside the boiler 100 is driven, water stored in the water tank 110 of the boiler 100 and residual water that remains in the hot water pipes 210-1 and 210-2 of the mat 200 are discharged to the outside through the residual water discharge flow path S1 and the residual water outlet 340 due to the suction action of the circulating pump 120. In this case, an additional discharge hose may be connected to the residual water outlet 340. Because air is introduced into the residual water removing connector 300 through the air inlet 350, the occurrence of a negative pressure caused by the suction action of the circulating pump 120 is prevented so that residual water suction and discharge operations can be smoothly performed.

Solid arrows in FIG. 5B represent a flow direction of residual water, and dotted arrows in FIG. 5B represent a flow direction of air.

When discharge of residual water through the residual water outlet 340 is finished, the driving of the circulating pump 120 is stopped so that the task of discharging residual water in the hot water mat is finished.

Hereinafter, a configuration and an operation of an apparatus for removing residual water in a hot water mat according to another embodiment of the present invention will be described with reference to FIG. 6.

The apparatus for removing residual water in the hot water mat according to another embodiment of the present invention, the hot water mat including a boiler 100 for supplying hot water by heating water and a mat 200 in which heating is performed by using hot water heated by the boiler 100 as a heat source, includes a circulating pump 120 provided inside the boiler 100 and pumping water to be circulated between the boiler 100 and the mat 200, a boiler connector 140 including a boiler-side discharge connector 141 and boiler-side water return connectors 142 and 143, which are connected to the boiler 100, and a mat connector 220-1 including a mat-side discharge connector 221 and mat-side water return connectors 222 and 223, which are connected to the mat 200. The boiler-side discharge connector 141 or the mat-side discharge connector 221 includes a gate 226 that opens/closes a flow path inside the boiler-side discharge connector 141 or the mat-side discharge connector 221, a residual water outlet 227 disposed at one side of the gate 226, and a first opening/closing valve 227a that opens/closes the residual water outlet 227. The boiler-side discharge connector 141 or the mat-side discharge connector 221 may include an air inlet 228 disposed at the other side of the gate 226 and a second opening/closing valve 228a that opens/closes the air inlet 228.

FIG. 6 illustrates an embodiment in which the gate 226, the residual water outlet 227, the first opening/closing valve 227a, the air inlet 228 and the second opening/closing valve 228a are provided in the mat-side discharge connector 221.

During the use of the hot water mat, the gate 226 is located so that a flow path inside the mat-side discharge connector 221 is opened, and the residual water outlet 227 is closed by the first opening/closing valve 227a, and the air inlet 228 is closed by the second opening/closing valve 228a.

When removing residual water in the hot water mat, the gate 226 is located so that an intermediate portion of a flow path inside the mat-side discharge connector 221 is blocked, as illustrated in FIG. 6, and the residual water outlet 227 is opened by the first opening/closing valve 227a, and the air inlet 228 is opened by the second opening/closing valve 228a. When the circulating pump 120 is driven, because residual water is discharged by passing through the boiler-side discharge connector 141 and the residual water outlet 227, and air is introduced into the residual water removing connector 300 through the air inlet 350, the occurrence of a negative pressure caused by the suction action of the circulating pump 120 is prevented so that residual water suction and discharge operations can be smoothly performed.

According to the current embodiment, in comparison with the above-described embodiment, a configuration of the residual water removing connector 300 is omitted, and in order to have a similar function to that of the residual water removing connector 300, the boiler-side discharge connector 141 or the mat-side discharge connector 221 includes the gate 226, the residual water outlet 227, the first opening/closing valve 227a, the air inlet 228, and the second opening/closing valve 228a so that the configuration of the apparatus can be further simplified.

As described above, according to the present invention, residual water that remains in a hot water mat can be conveniently and rapidly removed, and a circulating pump provided in the boiler is used so that the configuration of an apparatus for removing residual water can be simplified, and residual water is automatically removed using the circulating pump and furthermore, when a boiler connector and a mat connector are connected and separated so as to remove residual water, the leakage of hot water is prevented so that the risk of suffering low-temperature burns that may occur during the leakage of hot water is prevented and a residual water removing task can be safely performed.

In an apparatus for removing residual water in a hot water mat using a circulating pump according to an embodiment of the present invention, residual water in the hot water mat is removed by connecting a residual water connector between a boiler connector and a mat connector and driving the circulating pump provided in the boiler so that a residual water removal operation can be conveniently and rapidly performed.

In addition, because residual water in the boiler and the mat can be removed using the circulating pump which is an intrinsic power source provided in the boiler of the hot water mat, the configuration of the apparatus for removing residual water is simplified, and costs for operating the apparatus for removing residual water can be reduced.

In addition, residual water is automatically removed using the circulating pump and furthermore, the boiler connector and the mat connector include a first valve and a second valve for preventing the leakage of residual water so that, when the boiler connector and the mat connector are separated from each other so as to remove residual water, the occurrence of the leakage is securely eliminated so that the risk of a low-temperature burn caused by the leakage of hot water can be prevented.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. An apparatus for removing residual water in a hot water mat, the hot water mat including a boiler (100) configured to supply hot water by heating water and a mat (200) in which heating is performed by using hot water heated by the boiler (100) as a heat source, the apparatus comprising:
   a circulating pump (120) provided in the boiler (100) and configured to pump water to be circulated between the boiler (100) and the mat (200);
   a boiler connector (140) including a boiler-side discharge connector (141) and boiler-side water return connectors (142, 143), which are connected to the boiler (100);
   a mat connector (220) including a mat-side discharge connector (221) and mat-side water return connectors (222, 223), which are connected to the mat (200); and
   a residual water removing connector (300) coupled between the boiler connector (140) and the mat connector (220) and including a residual water outlet (340) through which water flowing through the boiler-side discharge connector (141) is discharged through an operation of the circulating pump (120).

2. The apparatus of claim 1, wherein an air inlet (350) is formed in the residual water removing connector (300) and communicates with the mat-side discharge connector (221).

3. The apparatus of claim 2, wherein the residual water removing connector (300) comprises:
   a discharge and air inlet (310) connected between the boiler-side discharge connector (141) and the mat-side discharge connector (221) and having the residual water outlet (340) and the air inlet (350) disposed therein; and
   return portions (320, 330) connected between the boiler-side water return connectors (142, 143) and the mat-side water return connectors (222, 223) and configured to provide a flow path for water returning to the boiler (100) from the mat (200).

4. The apparatus of claim 3, wherein a residual water discharge flow path (Si) that communicates with the boiler-side discharge connector (141) and the residual water outlet (340), and an air inlet flow path (S2) that communicates with the air inlet (350) and the mat-side discharge connector (221) are formed inside the discharge and air inlet (310).

5. The apparatus of claim 4, wherein a barrier wall (370) configured to block fluid communication between the residual water discharge flow path (S1) and the air inlet flow path (S2) is provided inside the discharge and air inlet (310).

6. The apparatus of claim 1, wherein the boiler connector (140) comprises a first valve (144) that opens a flow path inside the boiler connector (140) in a state in which the boiler connector (140) is coupled to the mat connector (220) or the residual water removing connector (300) and that closes the flow path inside the boiler connector (140) in a state in which the boiler connector (140) is separated from the mat connector (220) or the residual water removing connector (300).

7. The apparatus of claim 1, wherein the mat connector (220) comprises a second valve (225) that opens a flow path inside the mat connector (220) in a state in which the mat connector (220) is coupled to the boiler connector (140) or the residual water removing connector (300) and that closes the flow path inside the mat connector (220) in a state in which the mat connector (220) is separated from the boiler connector (140) or the residual water removing connector (300).

8. The apparatus of claim 1, wherein a connection portion between the boiler connector (140) and the residual water removing connector (300) comprises a first connector detachable portion (360) that is elastically supported to be engaged with the boiler connector (140) and the residual water removing connector (300) when the boiler connector (140) and the residual water removing connector (300) are coupled to each other and that is operated so that the engagement between the boiler connector (140) and the residual water removing connector (300) is released by a pressing operation of a user when the boiler connector (140) and the residual water removing connector (300) are separated from each other.

9. The apparatus of claim 1, wherein a connection portion between the residual water removing connector (300) and the mat connector (220) comprises a second connector detachable portion (224) that is elastically supported to be engaged with the residual water removing connector (300) and the mat connector (220) when the residual water removing connector (300) and the mat connector (220) are coupled to each other, and that is operated so that the engagement between the residual water removing connector (300) and the mat connector (220) is released by a pressing operation of the user when the residual water removing connector (300) and the mat connector (220) are separated from each other.

10. An apparatus for removing residual water in a hot water mat, the hot water mat including a boiler (100) for supplying hot water by heating water and a mat (200) in which heating is performed by using hot water heated by the boiler (100) as a heat source, the apparatus comprising:
a circulating pump (120) provided in the boiler (100) and configured to pump water to be circulated between the boiler (100) and the mat (200);
a boiler connector (140) including a boiler-side discharge connector (141) and boiler-side water return connectors (142, 143), which are connected to the boiler (100); and
a mat connector (220-1) including a mat-side discharge connector (221) and mat-side water return connectors (222, 223), which are connected to the mat (200),
wherein the boiler-side discharge connector (141) or the mat-side discharge connector (221) comprises a gate (226) that opens/closes a flow path inside the boiler-side discharge connector (141) or the mat-side discharge connector (221), a residual water outlet (227) disposed at one side of the gate (226) through which water flowing is discharged through an operation of the circulating pump (120), and a first opening/closing valve (227*a*) that opens/closes the residual water outlet (227).

11. The apparatus of claim 10, wherein the boiler-side discharge connector (141) or the mat-side discharge connector (221) comprises an air inlet (228) disposed at the other side of the gate (226) and a second opening/closing valve (228*a*) that opens/closes the air inlet (228).

\* \* \* \* \*